United States Patent
Harford et al.

(10) Patent No.: US 6,899,884 B2
(45) Date of Patent: *May 31, 2005

(54) VACCINE AGAINST MUMPS CONTAINING A JERYL-LYNN VIRUS STRAIN

(75) Inventors: Nigel Maurice Harford, Overijse (BE); Brigitte Desiree Alberte Colau, Genval (BE); Jean Didelez, Court-St-Etienne (BE)

(73) Assignee: SmithKline Beecham Biologicals, s.a., Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 10/699,751

(22) Filed: Nov. 3, 2003

(65) Prior Publication Data

US 2004/0120969 A1 Jun. 24, 2004

Related U.S. Application Data

(60) Continuation of application No. 10/213,965, filed on Aug. 7, 2002, now Pat. No. 6,656,476, which is a continuation of application No. 09/748,343, filed on Dec. 22, 2000, now abandoned, which is a continuation of application No. 09/441,479, filed on Nov. 17, 1999, now abandoned, which is a division of application No. 08/649,654, filed as application No. PCT/EP94/03801 on Nov. 15, 1994, now Pat. No. 6,024,962.

(30) Foreign Application Priority Data

Nov. 19, 1993 (GB) ............................................. 9323820
Mar. 31, 1994 (GB) ............................................. 9406480

(51) Int. Cl.$^7$ .................... A61K 39/295; A61K 39/165; A61K 39/20; A61K 39/245

(52) U.S. Cl. ................................. 424/202.1; 424/204.1; 424/212.1; 424/219.1; 424/230.1; 435/235.1; 435/239

(58) Field of Search ........................... 424/202.1, 212.1, 424/219.1, 230.1, 204.1; 435/235.1, 239

(56) References Cited

U.S. PATENT DOCUMENTS

| | | | | |
|---|---|---|---|---|
| 3,555,149 A | 1/1971 | Buynak et al. | .......... | 424/212.1 |
| 4,337,242 A | 6/1982 | Markus et al. | ................ | 424/89 |
| 6,024,962 A | 2/2000 | Harford et al. | .......... | 424/202.1 |

OTHER PUBLICATIONS

Afzal, et al., "The Jeryl Lynn vaccine strain of mumps virus is a mixture of two distinct isolates", (1993), Journal of General Virology, vol. 74, p. 917–920.

Takeuchi, et al., "Variations of Nucleotide Sequences and Transcription of the SH Gene among Mumps Virus Strains", (1991), Virology, vol. 181, No. 1, pp. 364–366.

Joklik et al., eds. Zinsser Microbiology, 20th Ed. Appleton & Lange, Norwalk, 1992, p. 744.

Elliott, et al., "Nucleotide Sequence of the Matrix, Fusion and Putative SH Protein Genes of Mumps Virus and Their Deduced Amino Acid Sequences", Virus Research, vol. 12 pp. 61–75 (1989).

*Primary Examiner*—James Housel
*Assistant Examiner*—Michael McGraw
(74) *Attorney, Agent, or Firm*—William R. Majarian; Jason C. Fedon; Edward R. Gimmi

(57) ABSTRACT

A new mumps vaccine is presented, comprising a homogeneous pure isolate derived from the Jeryl-Lynn strain of mumps virus. In a preferred embodiment of the invention the vaccine produces higher seroconversion and anitbody titres than know commercial vaccines.

6 Claims, 1 Drawing Sheet

Figure 1

Jeryl lynn isolate c DNA sequence over the SH gene and the SH HN intergenic region

TGAATCTCCTAGGGTCGTAACGTCTCGTGACCCTGCCGTCGCACTATGCC
GGCAATCCAACCTCCCTTATACCTAACATTTCTAGTGCTAATCCTTCTCT
ATCTCATCATAACCCTGTATGTCTGGACTATATTGACTATTAACTATAAG
ACGGCGGTGCGATATGCAGCACTGTACCAGCGATCCTTCTCTCGCTGGGG
TTTTGATCACTCACTCTAGAAAGATCCCCAATTAGGACAAGTCCCGATCC
GTCACGCTAGAACAAGCTGCATTCAAATGAAGCTGTGCTACCATGAGACA
TAAAGAAAAAAGCAAGCCAGAACAAACCTAGGATCATAACACAATACAGA
ATATTAGCTGCTATCACAACTGTGTTCCGGCCACTAAGAAAAT
□

VACCINE AGAINST MUMPS CONTAINING A JERYL-LYNN VIRUS STRAIN

This is a continuation of application Ser. No. 10/213,965 filed 7 Aug. 2002, now U.S. Pat. No. 6,656,476, which is a continuation of application Ser. No. 09/748,343 filed 22 Dec. 2000, now abandoned, which is a continuation of application Ser. No. 09/441,479 filed 17 Nov. 1999, now abandoned, which is a divisional of application Ser. No. 08/649,654 filed 13 May 1996, now U.S. Pat. No. 6,024,962, which is the §371 National Stage Entry of PCT/EP94/03801 filed 15 Nov. 1994.

Mumps is essentially a disease of childhood, which normally presents itself with only minor symptoms. However, in certain cases the clinical consequences of mumps infection are serious. For example, mumps is the most common cause of meningoencephalitis in children under 15 years of age in the UK, and a cause of permanent sensorineural deafness in childhood. Although 30–40% of natural mumps infection are symptomless, the very fact that salivary gland involvement can be unpleasant and that in the adult population mumps can cause 1st trimester abortions and orchitis of men as well as the neurological complications noted above, has led, in many countries, to the adoption of mass vaccination programs.

Mumps virus belonging to Paramyxoviridae is constituted by a single strand genomic RNA of the minus sense and is about 15,3 kb with the gene order 3' N-P-M-F-SH-HN-L5' (N-nucleocapsid protein, P=phosphoprotein, M=matrix protein, F=fusion protein, SH=potentially expressed as small hydrophobic protein, HN-haemagglutinin neuraminidase, L=large protein). Among various mumps strains, Jeryl-Lynn (B-level) is a live attenuated variant which has been characterised by sequence analysis of the F,P,HN,M genes.

Until recently, two mumps virus strains have been approved for vaccination against Mumps. These are Urabe Am 9 and Jeryl-Lynn. However in September 1992 the Urabe strain was withdrawn following a reported incidence of unacceptable level of side effects [European Journal of Pediatrics (1993) 152:387].

The Jeryl-Lynn strain has been sold commercially by Merck Sharp and Dohme for many years under the trade name "MumpsVax". The Jeryl-Lynn strain was obtained from a clinical sample of a patient suffering from mumps, by amniotic inoculation into embryonated hen's eggs (Proc. Soc. Exptl. Biol. Med. 123 (3) (1966)).

Afzal et al recently reported (J. of Gen. Virology 1993 74 917) that the Jeryl-Lynn strain used in mumps vaccines in the UK is in fact a mixture of two viruses, named JL-2 and JL-5.

Takeuchi et al Virology (1991) 181 p364–366 report that among different mumps strains there can be substantial nucleotide sequence variation at the SH gene level.

Afzal et al have emphasised that the present commercially available vaccine "Mumps Vax" is made under carefully controlled conditions including a cell bank and passage limits and which are likely to preserve the proportion of the two variants from batch to batch. However with further passaging of the Jeryl-Lynn strain there is no guarantee that this balance between the two variants will be retained. Moreover it is difficult to assess the proportion of the two variants in any given batch of vaccine.

The present inventors have surprisingly identified a yet further isolate which differs from both JL-2 and JL-5 of Afzal et al. The difference was determined by nucleotide sequence analysis of the SH gene and regions surrounding it, more particularly the nontranslated intercistronic region 3' to the SH coding sequence and 5' to the HN gene. This isolate in clinical trials induces a higher zero conversion and have highest geometric mean titre of mumps antibody than the commercially available mumps vaccine.

Accordingly the present inventors provide an attenuated Jeryl-Lynn mumps strain containing the nucleotide sequence as set forth in FIG. 1. This sequence encodes the SH gene and the N terminus of the HN gene. The strain is herein referred to as SBB JL-1.

In FIG. 1 there is shown the c DNA sequence of the JL-1 mumps virus isolate over the SH gene coding and SH-HN intergenic regions.

The present invention also provides a mumps vaccine comprising a substantially homogenous immunogenic Jeryl-Lynn isolate.

By substantially homogenous it is meant that the isolate is not contaminated with more than 10%, and preferably less than 5% and most preferably less than 1% of another Jeryl-Lynn isolate as defined by the sequence of the region set forth above. In a preferred embodiment of the invention, the vaccine contains a pure homogenous Jeryl-Lynn isolate i.e. devoid of any contamination with other Jeryl-Lynn mumps isolates which differ within the region set forth in FIG. 1.

In one embodiment of the invention there is provided a vaccine comprising homogenous SBB JL-1 devoid of contamination with JL-2.

The pure isolate does not suffer from the disadvantages of potential batch to batch variation between substrains and provides a product which is easier to ensure will meet consistent quality guidelines.

Homogenous Jeryl-Lynn according to the invention may be obtained by passaging commercially available Mumps-Vax on Chick Embryo Fibroblast (CEF) cells, and selecting pure cultures by either limit dilution and examination of resulting isolates or by individual plaque isolation. Other suitable cell lines include Vero cells and MRC5 cells. This requires that methods are available for detection of minor proportions of a known variant virus within a population. Such examination methods include the Maprec assay proposed by Chumakov et al for attenuated polio virus (WO 92/07958 and PNAS 1991, 88; 199–203), and direct sequencing of viral plaques and differential hybridization of viral plaques.

The vaccine of the invention may advantageously contain other components, such as attenuated measles virus, and/or attenuated rubella virus, killed or subunits thereof for providing protection against measles and/or rubella infections. Trivalent mumps measles and rubella vaccines are well known in the art and the present mumps isolate would be formulated in a trivalent vaccine in an analogous manner to those vaccines already available. Additionally or alternatively the vaccine of the invention may contain a live Varicella Zoster attenuated virus for providing protection against varicella (chicken pox) or Zoster (shingles). In a preferred embodiment the Varicella Zoster virus will be the Oka strain as disclosed by Andre F E Postgraduate MED J. (1985) 61(Suppl. 4), 113–120 or Veskari T et al Acta paediatr. Scand. 80: 1051–1057, 1991. Preferably the vaccine of the invention will be quadrivalent and provide protection against mumps, rubella measles and varicella zoster viruses.

The invention also provides a process for preparing a whole virus vaccine, for example by freeze drying the virus in the presence of suitable stabilisers or admixing the strain according to the invention with a suitable carrier or adjuvant.

It may also be advantageous to formulate the strain of the invention in liposomes or with carrier particles. Alternatively or in addition immunostimulants such as 3 de-O- acyl monophosphoryl Lipid A (Ribi Immunochem) or the saponin derivative QS21 (Cambridge Biotech) may be included in the formulation.

In a further aspect, the invention provides a method of treating mumps infection in humans, which method comprises administering to a human subject in need thereof an immunologically effective dose of the vaccine according to the invention.

The mode of administration of the vaccine of the invention may be any suitable route which delivers an immunoprotective amount of the strain and other immunogenic component of the vaccine to the subject. However, the vaccine is preferably administered parenterally via the intramuscular or deep subcutaneous routes. Other modes of administration may also be employed, where desired, such as oral administration or via other parenteral routes, i.e., intradermally, intranasally, or intravenously.

The appropriate immunoprotective and non-toxic dose of such vaccine can be determined readily by those skilled in the art, i.e., the appropriate immunoprotective and non-toxic amount of the strain of this invention contained in the vaccine of this invention may be in the range of the effective amounts of antigen in conventional whole virus vaccines. It will be understood, however, that the specific dose level for any particular patient will depend upon a variety of factors including the age, general health, sex, and diet of the patient; the time of administration; the route of administration; synergistic effects with any other drugs being administered; and the degree of protection being sought. Of course, the administration can be repeated at suitable intervals if necessary. Typically in a monovalent presentation at least 3.7 log TC1D50 of virus and more generally 4.5 log TC1D50 will be present per dose. In a trivalent mumps, measles, rubella vaccine the mumps component will be present at around 4.8 log TC1D50 to offset the interference of the other two viral components.

EXAMPLES

1) Initial Sequencing of the SH Gene

Commercial MumpsVax virus was passaged on confluent monolayers of Vero cells grown in 25 cm$^2$ flasks with dMEM Biorich medium (50/50 v/v) with 0.5% foetal calf serum using about 3.0 log TC1D50 as inoculum. The infected cells were recovered after 7 days incubation at 34° C. and the RNA extracted by the method of Ferré and Garduno (Nucleic Acids Research 1989, 17; 2141) into 100 mcl of water treated with diethylpyrocarbonate for 5 minutes at 100° C. 5 mcl of this extract was reverse transcribed by adding the following reagents: RNAsin 40 units (Boehringer Mannheim, Germany), 4 mcl of 5× concentrated reverse transcriptase buffer (Bethesda Research Labs,), 2 mcl of a mixture of the four deoxynucleotide triphosphates at 10 mM, 10 pmole of NH2 (SEQ ID NO:2) oligonucleotide primer, 1 mcl of Moloney murine leukemia virus (MMLV) reverse transcriptase (Bethesda Research Labs, 200 units per mcl) and water to a final volume of 20 mcl. Oligonucleotide NH2 has homology to the F gene of the Urabe strain of mumps virus. The mixture was incubated for 45 min at 37° C. and then heated for 5 min at 95° C. The cDNA was then amplified by two successive rounds of PCR reaction using oligonucleotides NH8 (SEQ ID NO:3) and NH14 (SEQ ID NO:4) as primers and using 1 mcl of a thousand/fold dilution of the first round reaction as starting material for the second round. Each PCR round consisted of 25 cycles of heating at 94° C. for 1 min, 53° C. for 1 min, 72° C. for 1 min. The PCR product corresponding to the SH gene was sequenced in both directions after further PCR amplification in the presence of fluorodideoxynucleotide terminators and either NH8 or NH14 as primers and analysis of the products on an Applied Biosystems automatic (373A DNA sequencer) sequencer according to the suppliers protocol and recommendations. Ambiguities were observed at a number of positions in the sequence and confirmed on both strands. The sequence obtained differed from that of Takeuchi et al (Virology 1991,181; 364–366) for Jeryl Lynn at 17 of 361 bases including 4 unassigned bases. The sequence further differed from part of that obtained by Afzal et al (J. Gen Virol. 1993, 74; 917–920) for their JL-5 isolate by 9 of 319 bases including 4 unassigned bases. Ambiguities were also observed when the same region was sequenced directly from 4.0 to 5.0 log TC1D50 MumpsVax virus recovered by ultracentrifugation, without prior passage on Vero cells, and after reverse transcription of viral RNA into cDNA with random primers followed by PCR amplification with oligonucleotides NH30bis (SEQ ID NO:9) and NH31bis (SEQ ID NO:10) as primers.

2) Cloning of the SH Gene

MumpsVax virus was used to infect Vero cells and total RNA was prepared as described above. The RNA was reverse transcribed using random primers and PCR amplified using oligonucleotides NH22 (SEQ ID NO:5) and NH23 (SEQ ID NO:6) as primers. (NH22 contains a HindIII restriction site within the primer and NH23 contains a BamHI restriction site within the primer to facilitate cloning of the amplified DNA fragment). The amplified DNA was restricted with HindIII and BamHI endonucleases and cloned into the vector pUC9. Eleven clones containing an insert corresponding to the mumps SH gene region were recovered. All eleven had a sequence corresponding to that of Takeuchi et al (loc cit). In addition five clones had a DdeI restriction site, absent in the six other clones. No insert corresponding to the JL-5 sequence was recovered. This result and the sequencing ambiguities suggested the the JL-2 variant virus defined by Afzal et al forms a substantial or easily detectable proportion of MumpsVax virus.

3) Passaging Directly from MumpsVax

MumpsVax virus was also passaged directly on Chicken Embryo Fibroblast (CEF) cells. Virus was recovered at the third passage from 5 different lots including the lot MJ05 used to prepare the lyophilized sample MJ05A42 for injection in animals. The 5 virus preparations were used to infect Vero cells and RNA was recovered and prepared for DNA sequencing by amplification with primers NH8 and NH14 table as described above except that random primers were used to prime the reverse transcriptase reaction. All 5 lots of virus displayed a sequence identical to that of JL-2 (Takeuchi et al) and without ambiguities.

To investigate this further the direct sequencing method on viral plaques was used as described above. The 5 lots were used to infect Vero cell cultures and obtain plaques which were processed for sequencing using NH30bis and NH31bis as primers. Of a total of 26 plaques tested for the 5 lots, 13 gave a sequence identical to Takeuchi et al for the JL-2 sequence, 5 gave a sequence very similar to JL-5 except for two base differences at positions 270 and 279 as shown in FIGS. 2 and 8 plaques gave sequences with ambiguities indicating a mixture of virus.

4) Direct Sequencing of Viral Plaques

Three dilutions of MumpsVax containing an estimated 100, 50 and 10 virus particles per 0.5 ml aliquot were used to infect confluent monolayers of Vero cells in 5 cm Petri dishes after removal of the medium and washing with DMEM Biorich 50:50 v/v medium (Biorich) without serum. Virus was allowed to adsorb during 30 minutes at 34° C. The cells were then covered with 5 ml of overlay agar held at 42° C. and containing 2.5 ml of dMEM Biorich medium with 0.5% FCS and 2.5 ml of 3% (w/v) low gelling temperature agarose. After solidification the agar layer was covered with 3 ml of dMEM Biorich medium with 0.5% foetal calf serum and incubated at 34° C. After 7 days incubation the viral plaques were visualized by removing the superficial liquid medium and adding 0.03% (w/v) neutral red solution and allowing this to diffuse for 1 hour. The liquid and agar was then removed and a dry nylon filter applied to the bottom of the dish with finger pressure. The filter was then wet with a few drops of 2×SSC and lifted. Virus was fixed to the filter by placing it on paper soaked in 2×SSC for 5 min and then on paper soaked in 2×SSC, 0.2% (w/v) sodium dodecyl sulphate for 30 min and then exposing the filters to UV light for three to five minutes. Twenty individual plaques were cut from the nylon filters and the piece of membrane was immersed in 100 mcl of water and 1 mcl of RNAsin (Boehringer Mannheim, 40 units) was, added before heating at 65° C. for 30 minutes. The 100 mcl of liquid was transferred to a fresh tube and the nucleic acids precipitated by adding 10 mcl of 3M sodium acetate followed by 250 mcl of ethanol. The mixture was held overnight at −20° C. or for 1 hour at −70° C. before centrifugation. The pellet was then dried. The material was then reverse transcribed by adding the following solutions to the pellet: 4 mcl 5× concentrated reverse transcriptase buffer (Bethesda Research Labs,) 2 mcl of 0.1M dithiothreitiol, 1 mcl of a mixture of deoxynucleotide triphosphates (Perkin Elmer-Cetus, 10 mM concentration), 1 mcl of N6 random primer oligonucleotides (New England Biolabs, concentration 100 mcg per ml) and 11 mcl of water. 1 mcl of MMLV reverse transcriptase was then added and the mixture incubated for 1 hour at 37° C. and then for 5 min at 95° C. The cDNA was then PCR amplified by taking 10 mcl of the above mixture and adding 500 ng of each of the oligonucleotide primers NH30bis and NH31bis, PCR buffer and 1 mcl of Stoffel DNA polymerase (Perkin Elmer-Cetus, concentration 10 ug mcl in 100 mcl final volume and heating the mixture for 30 cycles of 1 min at 95° C., 1 min at 60° C. and 1 min at 72° C. The resulting fragment was purified using a MagicPrep kit (Promega Biotech A7170,) according to the suppliers instructions. Sequencing was done after further asymmetric PCR amplification using either NH30bis or NH31bis as primers and fluorodideoxynucleotide terminators by a non-radioactive method on an Applied Biosystems (373A) automatic sequencer using the methods and reactants of the supplier. Of the twenty plaques from MumpsVax, 19 were found to differ by 11 of 275 bases from the JL-2 sequence of Takeuchi et al (loc cit) and by 2 bases from the JL-5 sequence of Afzal et al (loc cit). One plaque gave a sequence with ambiguities. This result suggested that MumpsVax may contain a variant or variants which differ in this region from the dominant JL-5 strain found by Afzal et al. The two bases differing between JL-5 and the plaques sequenced are at positions 270 and 279 and are located in the intergenic region between the SH and HN coding regions.

5) Plaque Hybridization

To attempt to determine more directly the proportion of the JL-5 and JL-2 type variants in MumpsVax and derivative cultures a plaque hybridization method was used. MumpsVax virus and the passaged virus of lot MJ05 were used to infect Vero cell monolayers and obtain plaques which were then lifted onto nylon membranes and the nucleic acids fixed as described above. The filters were prehybridized for 3 hours at 65° C. in 200 ml of the following solution: 5×SSC (SSC is 0.15M sodium chloride 0.01M sodium citrate pH 7.2), (10× concentrated Denhardts solution is: 0.2% w/v Ficoll 400, 0.2% bovine serum albumin, 0.2% polyvinyl chloride), 0.1% (w/v) sodium dodecyl sulphate, Salmon sperm DNA 50 mcg per ml. The filters were then hybridized with gentle agitation for 2.5 hours at 65° C. in 50 ml of a solution with the same composition as above and preheated to 65° C. and with the addition of the radioactive probe and cold competitor probe solution. The oligonucleotides used as variant specific probes were BC252 (SEQ ID NO:12) which hybridizes with JL-5 variants BC253 (SEQ ID NO:13) which hybridizes with JL-2 variants. The oligonucleotides were labelled with gamma $^{32}$P-ATP by kination in a solution of the following composition: 100 ng of the oligonucleotide to be labelled, 3 mcl of 10× concentrated kinase buffer (10× concentrated kinase buffer contains: 0.5M Tris —HCl pH 7.6, 0.1M MgCl2, 50 mM dithiothreitol, 1 mM spermidine and 1 mM EDTA pH 8.0), 3 mcl of $^{32}$P-ATP (Amersham International, 3000 Ci/nmole, 10 mCi/mcl) and 2 mcl of T4 polynucleotide kinase (Boehringer Mannheim,) made up to 30 mcl with sterile water. This mixture was incubated for 30 minutes at 37° C. and the reaction stopped by heating for 5 minutes at 95° C. Cold competitor oligonucleotide was then added at a (w/w) ratio of 100 to 1, that is 10 mcg of cold competitor oligonucleotide was added for every 100 ng of labelled probe, before adding the mixture to the hybridization solution. After hybridization the filters were washed once for 30 minutes at 65° C. in 100 ml of a solution with the same composition as the hybridization solution and then washed at 65° C. in two changes of 100 ml of a solution of the following composition: SSC 5×, 0.1% sodium dodecyl sulphate. The filters were then dried and exposed to X-ray film with an intensifying screen. When MumpsVax was examined by this technique a large excess of plaques hybridized with oligonucleotide BC252 specific for the JL-5 variant compared to the hybridization found with BC253. When lot MJ05 was examined, although there were approximately equal numbers of plaques hybridizing with both probes, relatively more plaques hybridized with BC253 than with BC252.

6) Isolation of Pure Jeryl Lynn Isolates

To recover pure isolates of the JL-5 and JL-2 variants, a sample of commercial MumpsVax (lot 92A06 from Merck Sharp and Dohme deposited at the Public Heath Laboratory Services, Porton Down, Wiltshire, UK under Accession No. Jeryl-Lynn Mumps Strain:V93110585 on 5th November, 1993) at a stated titre of 4–6 log TCID50 infections units was limit diluted and used to infect Chicken Embryo Fibroblast cells in 96 well microtiter plates at an estimated inoculum of 0.1 infections units per well. The plates were incubated 11 days at 34° C. to permit development of the virus. Seventeen wells of a total of 192 inoculated showed a cytopathic effect indicating viral growth and these were used to inoculate further cultures of CEF cells. The identity of the virus isolated was determined on this second passage material which titred about 4.9 log TCID50 by filtering the virus preparations through a 0.8 μm filter, centrifugation for 1 hour at 42,000 rpm and resuspension of the viral pellet with 100 mcl $H_2O$. One mcl of RNase inhibitor (Boehringer Mannheim, 40 units per mcl) was added and the mixture incubated for 30 minutes at 65° before addition of 1/10 volume 3 M Na Acetate (pH 4.5) followed by 2.5 volumes of ethanol. The material was allowed to precipitate overnight at −20° C. or for one hour at −70° C. before being centrifuged for 30 minutes at 4° C. in an Eppendorf bench-top centrifuge and the pellet dried.

Viral RNA recovered was reverse transcribed by adding 20 mcl of the following mixture to the pellet. 4 mcl of 5× core RT buffer (Bethesda Research Labs), 2 mcl of 10 nM deoxynucleotide triphosphate mixture (Perkin Elmer, Cetus), 1 mcl of random primers N6 (Biolabs, at 100 mcg/ML), 11 mcl of $H_{2O}$, 1 mcl of MMLV reverse transcriptase (Bethesda Research Labs). This mixture was incubated for 1 hour at 37° C. followed by 5 minutes at 95° C. to inhibit the reverse transcriptase. 10 mcl of the heated mixture was then subjected to PCR amplification in 100 mcl final volume with the primers NH30 bis and NH31bis using the following heading programme for 30 cycles: 1 minute at 95° C., 1 minute at 60° C., 1 minute at 72° C. The resulting fragments were purified by Magic Prep (Promega) according to the manufacturers' protocol.

The six isolates reacting only with the JL-5 probe were inoculated onto Vero cells to obtain plaques. These were lifted onto nylon membranes and the membranes hybridized with oligonucleotide BC252 and with oligonucleotide BC253, both labelled with $^{32}P$ by kination as described above. Hybridization was done n 5×SSC at 65° C. for 2.5 hours using about 100 ng of labelled oligonucleotides and 10 mcg of cold competitor oligonucleotide in a volume of 50 ml. About 200 plaques were tested for each isolate and none reacted with the JL-2 probe (oligonucleotide BC253). All plaques reacted with BC252.

One virus isolate, originating from well 9H2A of the micro titre plate and further identified as SBB strain JL-1 was taken through two further passages on CEF cells. After the last passage (4 passages from the original Mumps Vax material), the virus was used to infect Vero cells and to obtain plaques. These were lifted onto nylon membranes and tested by hybridization with oligonucleotides BC252 and BC253 which had been labelled with $^{32}P$ by kination. Over 2000 plaques were tested with the JL-2 specific probe BC253 and none was found to react with this. A lesser number of plaques was tested with oligonucleotide BC252 and all gave a positive reaction. Sequencing was performed directly on the virus pool of the JL-1 stain recovered at the fourth passage on CEF cells by centrifugation and ethanol precipitation of the virus followed by reverse transcription using random primers as described above. The cDNA was amplified by PCR reaction using oligonucleotides NH14 and BC265 as (SEQ ID NO:11) as primers and with the following heating programme: 1 minute at 94° C., 1 minute at 60° C., 1 minute at 72° C., for 30 cycles. The resulting DNA fragment was purified on a MagicPrep column (Promega Biotech) according to the suppliers' instructions and sequenced on an Applied Biosystems 373A automatic sequencer according to the manufacturers' instructions and using oligonucleotides NH14, BC265, NH 30 bis and NH31 bis as primers. The sequence shown in FIG. 1 was obtained. This sequence surprisingly differs from that obtained by Afzal et al for their JL-5 isolate at six positions in the intergenic region between the SH and HN coding regions as shown in FIG. 2. The JL-1 isolate therefore represents a further variant virus present in the MumpsVax preparation.

A second virus isolate, identified as $10H_5F$ which also reacted only with the JL-5 probe, was sequenced by infecting Vero cells with passage two virus, lifting a plaque onto a nylon membrane and performing sequencing after PCR amplification using NH14 and BC265 oligonucleotides as primers. This gave a sequence identical to that for 9H2A above and differing from the published JL-5 isolate sequence by 6 bases in the SH-HN intergenic region.

7) Immunogenicity

The immunogenicity of the JL-1 strain from Example 6 was tested in monkeys. A lyophilized JL-1 virus preparation, called MJ11A42, at the fourth passage from MumpsVax and harvested after 6 days growth at 34° C. on CEF cells and at a dose of of 4.2 log TCID50 was used to immunize a group of four African Green monkeys by subcutaneous injection. Three further groups of four monkeys were injected with: (a) MumpsVax at a concentration of 4.3 log TCID50; (b) with a lyophilized preparation, MJ21A42, at a concentration of 4.3 log TCID50 per dose from virus harvested after 9 days growth at 32° C. and derived from three direct passages of MumpsVax on CEF cells; (c) with a lyophilized preparation, MJ05A42, at a concentration of 4.2 TCID50 per dose from virus harvested after 7 days growth at 34° C. and derived from three direct passages of MumpsVax on CEF cells the passages being different from those for the MJ21A42 preparation.

Blood samples were taken before injection on day 0 and on days 28 and 42 after vaccination and tested for the presence of IgG antibodies to mumps virus using the commercial Enzygnost Anti-Parotitis Virus kit from Behring (Behringwerke AG, Marburg, Germany) as described by the supplier. As shown in Table 1 the preparation derived from the pure JL-1 strain induces a higher titre of anti-mumps virus antibodies in the animals than the other preparations, including MumpsVax. These sera were also tested at two-fold serial dilutions in a plaque reduction assay using MumpsVax as test virus. The sera from the animals injected with lot MJ11A42 gave a higher average reduction in the number of plaques compared to the other sera.

8) Clinical Studies

The JL-1 strain was further tested in a clinical trial with seronegative children of about 15 months of age. Trivalent measles, mumps and rubella vaccines were formulated and lyophilized using either pure JL-1 stain as the mumps component or with mumps virus derived by directly passaging Mumps Vax on CEF cells as in Example 6 above. Commercial M-M-R®II vaccine produced by Merck and Co Inc and obtainable from Merck Frossr Inc Kirkland, Quebec, Canada was also included in the trial; it contains the Jeryl-Lynn (B-level) strian as the mumps components.

The titres of mumps virus in the three vaccine preparations were measured as 4.5 log TCID doses for the vaccine lot number MJR111D42 containing the pure JL-1 strain, 4.7 log TCID doses for the vaccine lot number MJR121C42 containing the passaged MumpsVax virus and 4.5 log TCID doses for the lot number 80391 OU commercial M-M-R® II vaccine.

Blood samples were taken from the children before vaccination and at 42 days post vaccination.

The presence of IgG antibodies to mumps virus was tested using the same commercial kit described above in Example 6. As shown in Table 3 the pure JL-1 strain MMR vaccine induced both the highest seroconversion rate and gave the highest geometric mean titre of the three preparations.

TABLE 1

| Injection July 1993 | | Test ELISA mumps | | | | |
|---|---|---|---|---|---|---|
| Description | Monkey | day 0 | day 28 | AMT (arithmetic mean titre) | day 42 | AMT (arithmetic mean titre) |
| Pure JL-1 | KU542 | <230 | 3300 | | 2800 | |
| (MJ11 A42) | 544 | <230 | 4300 | | 4100 | |
| | 547 | <230 | 3300 | | 3900 | |
| | 551 | <230 | 2600 | 3375 | 2200 | 3250 |

TABLE 1-continued

| | | Test ELISA mumps | | | |
|---|---|---|---|---|---|
| Injection July 1993 | | | AMT (arithmetic | | AMT (arithmetic |
| Description | Monkey | day 0 | day 28 mean titre) | day 42 | mean titre) |
| (MJ21 A4) | 545 | <230 | 770 | 510 | |
| | 550 | <230 | 2300 | 2100 | |
| | 552 | <230 | 3300 | 2500 | |
| | 553 | <230 | 3500 | 2468 | 2900 | 2003 |
| MSD92A06 | 548 | <230 | 3100 | 690 | |
| Mump Vax | 549 | <230 | 890 | 2300 | |
| | 554 | <230 | 600 | 490 | |
| | 555 | <230 | 1700 | 1573 | 1300 | 1195 |
| (MJ05A42) | 556 | <230 | 1000 | 1400 | |
| | 557 | <230 | 3100 | 2600 | |
| | 558 | <230 | <230 | <230 | |
| | 559 | <230 | 750 | <1270 | 440 | <1168 |

TABLE 2

OLIGONUCLEOTIDE UTILISED

| Code | Sequence (5'—3') |
|---|---|
| NH 2 | GTA GCA CTG GAT GGA |
| NH 8 | TCT GTG TTG TAT TGT GAT CC |
| NH 14 | GTC GAT GAT CTC ATC AGG TAC |
| NH 22 | CGG TAG AAG CTT GTC GAT GAT CTC ATC AGG TAC |
| NH 23 | CGC TGA GGA TCC TCT GTG TTG TAT TGT GAT CC |

TABLE 2-continued

OLIGONUCLEOTIDE UTILISED

| Code | Sequence (5'—3') |
|---|---|
| NH 30 | ATC TCC TAG GGT CGT AAC |
| NH 31 | TTT GGA TGC AGC TTG TTC |
| NH 30bis | AAT CTC CTA GGG TCG TAA CGT CTC GTG A |
| NH 31bis | TTT GAA TGC AGC TTG TTC TAG CGT |
| BC 265 | CCG ACA TTA TGA ATA GTT TCG AGG GCT CC |
| BC 252 | ATA TCG CAC CGC CGT CTT ATA GTT AAT AGT C |
| BC 253 | ATA CCG AAC CGC CGT ATT ATG GTT AAT GGT C |

TABLE 3

SEROCONVERSION AND GEOMETRIC MEAN TITRE (GMT) TO MUMPS VIRUS IN SERONEGATIVE SUBJECTS

| Vaccine | Timing | Number | Number seroconverting | GMT |
|---|---|---|---|---|
| MJR111D42 | pre | 15 | 0 | — |
| | day 42 | 15 | 15 | 1434 |
| MJR121C42 | pre | 13 | 0 | — |
| | day 42 | 13 | 11 | 971 |
| 803910U | pre | 17 | 0 | — |
| | day 42 | 17 | 16 | 1247 |

What is claimed is:

1. A combined vaccine comprising a substantially homogeneous immunogenic Jeryl-Lynn isolate, an attenuated measles virus, an attenuated rubella virus, and an agent for protection against varicella zoster infection, the vaccine not contaminated with more than 10% of another Jeryl-Lynn isolate.

2. A combined vaccine comprising a substantially homogeneous immunogenic Jeryl-Lynn isolate, a killed measles virus, a killed rubella virus, and an agent for protection against varicella zoster infection, the vaccine not contaminated with more than 10% of another Jeryl-Lynn isolate.

3. A combined vaccine comprising a substantially homogeneous immunogenic Jeryl-Lynn isolate, a subunit of a measles virus, a subunit of a rubella virus, and an agent for protection against varicella zoster infection, the vaccine not contaminated with more than 10% of another Jeryl-Lynn isolate.

4. A method of inducing immunity in a mammal to measles, mumps, rubella and varicella zoster virus infections comprising administration to the mammal of an effective amount of a vaccine according to claim 1.

5. A method of inducing immunity in a mammal to measles, mumps, rubella and varicella zoster virus infections comprising administration to the mammal of an effective amount of a vaccine according to claim 2.

6. A method of inducing immunity in a mammal to measles, mumps, rubella and varicella zoster virus infections comprising administration to the mammal of an effective amount of a vaccine according to claim 3.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 393 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (B) STRAIN: Mumps Virus
      (C) INDIVIDUAL ISOLATE: JL-1

(xi) SEQUENCE DESCRIPTION: SEQ ID NO: 1:

```
TGAATCTCCT AGGGTCGTAA CGTCTCGTGA CCCTGCCGTC GCACTATGCC GGCAATCCAA      60

CCTCCCTTAT ACCTAACATT TCTAGTGCTA ATCCTTCTCT ATCTCATCAT AACCCTGTAT     120

GTCTGGACTA TATTGACTAT TAACTATAAG ACGGCGGTGC GATATGCAGC ACTGTACCAG     180

CGATCCTTCT CTCGCTGGGG TTTTGATCAC TCACTCTAGA AAGATCCCCA ATTAGGACAA     240
```

-continued

```
GTCCCGATCC GTCACGCTAG AACAAGCTGC ATTCAAATGA AGCTGTGCTA CCATGAGACA      300

TAAAGAAAAA AGCAAGCCAG AACAAACCTA GGATCATAAC ACAATACAGA ATATTAGCTG      360

CTATCACAAC TGTGTTCCGG CCACTAAGAA AAT                                  393
```

(2) INFORMATION FOR SEQ ID NO: 2:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Mumps
        (C) INDIVIDUAL ISOLATE: NH2

(xi) SEQUENCE DESCRIPTION: SEQ ID NO: 2:

```
GTAGCACTGG ATGGA                                                       15
```

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Mumps
        (C) INDIVIDUAL ISOLATE: nh8

(xi) SEQUENCE DESCRIPTION: SEQ ID NO: 3:

```
TCTGTGTTGT ATTGTGATCC                                                  20
```

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (B) STRAIN: Mumps (vii) IMMEDIATE SOURCE:
        (B) CLONE: Nh14

(xi) SEQUENCE DESCRIPTION: SEQ ID NO: 4:

```
GTCGATGATC TCATCAGGTA C                                                21
```

(2) INFORMATION FOR SEQ ID NO: 5:

-continued (i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(B) STRAIN: Mumps
(C) INDIVIDUAL ISOLATE: nh22

(xi) SEQUENCE DESCRIPTION: SEQ ID NO: 5:

CGGTAGAAGC TTGTCGATGA TCTCATCAGG TAC 33

(2) INFORMATION FOR SEQ ID NO: 6:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(B) STRAIN: Mumps
(C) INDIVIDUAL ISOLATE: NH23

(xi) SEQUENCE DESCRIPTION: SEQ ID NO: 6:

CGCTGAGGAT CCTCTGTGTT GTATTGTGAT CC 32

(2) INFORMATION FOR SEQ ID NO: 7:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(B) STRAIN: Mumps (vii) IMMEDIATE SOURCE:
(B) CLONE: nh30

(xi) SEQUENCE DESCRIPTION: SEQ ID NO: 7:

ATCTCCTAGG GTCGTAAC 18

(2) INFORMATION FOR SEQ ID NO: 8:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

```
    (iii) HYPOTHETICAL: NO (iv) ANTI-SENSE: NO (vi) ORIGINAL SOURCE:
          (B) STRAIN: Mumps
          (C) INDIVIDUAL ISOLATE: NH31

(xi) SEQUENCE DESCRIPTION: SEQ ID NO: 8:

TTTGGATGCA GCTTGTTC                                                18

(2) INFORMATION FOR SEQ ID NO: 9:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (B) STRAIN: Mumps (vii) IMMEDIATE SOURCE:
          (B) CLONE: NH30bis (xi) SEQUENCE DESCRIPTION: SEQ ID NO: 9:

AATCTCCTAG GGTCGTAACG TCTCGTGA                                     28

(2) INFORMATION FOR SEQ ID NO: 10:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (B) STRAIN: Mumps
          (C) INDIVIDUAL ISOLATE: nh31bis (xi) SEQUENCE DESCRIPTION: SEQ ID NO: 10:

TTTGAATGCA GCTTGTTCTA GCGT                                         24

(2) INFORMATION FOR SEQ ID NO: 11:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (B) STRAIN: mumps
          (C) INDIVIDUAL ISOLATE: bc256
```

-continued (xi) SEQUENCE DESCRIPTION: SEQ ID NO: 11:

CCGACATTAT GAATAGTTTC GAGGGCTCC                29

(2) INFORMATION FOR SEQ ID NO: 12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Mumps (vii) IMMEDIATE SOURCE:
        (B) CLONE: bc252

(xi) SEQUENCE DESCRIPTION: SEQ ID NO: 12:

ATATCGCACC GCCGTCTTAT AGTTAATAGT C               31

(2) INFORMATION FOR SEQ ID NO: 13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Mumps
        (C) INDIVIDUAL ISOLATE: BC253

(xi) SEQUENCE DESCRIPTION: SEQ ID NO: 13:

ATACCGAACC GCCGTATTAT GGTTAATGGT C               31